United States Patent
Stadler et al.

(10) Patent No.: US 10,512,781 B2
(45) Date of Patent: Dec. 24, 2019

(54) REDUCTION OR ELIMINATION OF PACE POLARIZATION EFFECTS

(71) Applicant: Medtronic, Inc., Minneapolis, MN (US)

(72) Inventors: Robert W. Stadler, Shoreview, MN (US); Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/989,927

(22) Filed: May 25, 2018

(65) Prior Publication Data
US 2018/0272135 A1    Sep. 27, 2018

Related U.S. Application Data

(62) Division of application No. 14/216,100, filed on Mar. 17, 2014, now Pat. No. 9,981,136.

(51) Int. Cl.
| | |
|---|---|
| *A61N 1/37* | (2006.01) |
| *A61B 5/046* | (2006.01) |
| *A61N 1/362* | (2006.01) |
| *A61N 1/368* | (2006.01) |

(52) U.S. Cl.
CPC .............. *A61N 1/371* (2013.01); *A61B 5/046* (2013.01); *A61N 1/3624* (2013.01); *A61N 1/3684* (2013.01); *A61N 1/3716* (2013.01); *A61N 1/3622* (2013.01)

(58) Field of Classification Search
CPC ................................ A61N 1/371; A61B 5/046
USPC .............................................. 607/19, 27, 28
See application file for complete search history.

(56) References Cited

U.S. PATENT DOCUMENTS

| | | | |
|---|---|---|---|
| 4,428,378 | A | 1/1984 | Anderson |
| 5,052,388 | A | 10/1991 | Sivula |
| 5,999,850 | A | 12/1999 | Dawson et al. |
| 7,089,049 | B2 | 8/2006 | Kerver |
| 7,187,972 | B1 | 3/2007 | Fain et al. |
| 7,684,863 | B2 | 3/2010 | Parikh |

(Continued)

FOREIGN PATENT DOCUMENTS

EP    1110580 A2    6/2001

OTHER PUBLICATIONS

(PCT/US2014/028108) PCT Notification of Transmittal of the International Search Report and the Written Opinion of the International Searching Authority.

*Primary Examiner* — Nadia A Mahmood (57) ABSTRACT

The present disclosure relates to cardiac evoked response detection and, more particularly, reducing polarization effects in order to detect an evoked response following delivery of a stimulation pulse. An implantable medical device (IMD) is configured to deliver a ventricular pacing pulse. A signal is sensed in response to the ventricular pacing stimulus. A window is placed over the sensed signal to obtain a set of data from the signal after a paced event. The set of data extracted from the sensed signal comprises a maximum amplitude, a maximum time associated with the maximum amplitude, a minimum amplitude, and a minimum time associated with the minimum amplitude. Responsive to processing the extracted data, the window is delayed to avoid polarization effects. A determination is then made as to whether the ventricular pacing stimulus is capturing the paced ventricle in response to determining whether the maximum time is greater than the minimum time.

21 Claims, 6 Drawing Sheets

(56) References Cited

U.S. PATENT DOCUMENTS

| | | |
|---|---|---|
| 8,750,998 B1 | 6/2014 | Ghosh |
| 9,002,454 B2 | 4/2015 | Ghosh |
| 2004/0215259 A1 | 10/2004 | Krig et al. |
| 2004/0215274 A1 | 10/2004 | Kerver et al. |
| 2011/0319951 A1 | 12/2011 | More et al. |
| 2012/0165897 A1 | 6/2012 | Enrooth et al. |
| 2014/0277245 A1 | 9/2014 | Lu et al. |

REDUCTION OR ELIMINATION OF PACE POLARIZATION EFFECTS

CROSS-REFERENCE TO PRIOR APPLICATION

The present application is a divisional of U.S. application Ser. No. 14/216,100, filed Mar. 17, 2014, now allowed. The disclosure of the above application is incorporated herein by reference in its entirety.

FIELD

The present disclosure relates to cardiac evoked response detection and, more particularly, reducing polarization effects in order to detect an evoked response following delivery of a stimulation pulse.

BACKGROUND

Implantable medical devices (IMDs), such as pacemakers, determine whether capture has occurred in response to a stimulation pulse in order to determine the effectiveness of the pacing therapy administered to the patient. The term "capture" generally refers to a cardiac depolarization and contraction of the heart in response to a stimulation pulse applied by the implantable medical device. To determine whether a stimulation pulse is capturing a ventricle, an IMD monitors the cardiac activity of a patient to search for presence of an evoked response following the stimulation pulse. The evoked response is an electrical event that occurs in response to the application of the stimulation pulse to the heart. The cardiac activity of the patient is monitored through the medical device by tracking stimulation pulses delivered to the heart and examining, via one or more electrodes on leads deployed within the heart, electrical activity signals that occur concurrently with depolarization or contraction of the heart.

The evoked response is often difficult to detect due to a pace polarization artifact, which is also referred to as a post-pace polarization artifact or a pace polarization signal. Pace polarization effects or artifacts are present on the sensing electrode employed to sense the electrical activity of the heart. Polarization of the pacing electrode is caused by accumulation of charge on an interface between the electrode and the cardiac tissue of the heart during delivery of a stimulation pulse.

Differentiating between pace polarization artifacts and evoked response signals can be problematic. For example, residual pace polarization artifacts typically have high amplitudes even when evoked response signals do occur. Additionally, a patient exhibiting a fast ventricular rate causes repolarization (i.e. T wave) to be pushed closer to depolarization (i.e. QRS wave). Consequently, differentiating between pace polarization artifacts and evoked response signals becomes even more difficult, if not impossible, using a conventional pacemaker or pacer cardioverter defibrillator (PCD) sense amplifier employing linear frequency filtering techniques. Additionally, the generated polarization artifact may result in the pacemaker identifying a false evoked response, which in turn leads to missed heartbeats. Furthermore, the polarization signal can cause the pacemaker to fail to detect an evoked response that is in fact present.

A variety of techniques have been used to reduce pace polarization artifacts. For example, U.S. Pat. No. 7,089,049 to Kerver et al. is configured to remove polarization artifacts from electrical activity signals in order to improve detection of an evoked response. More specifically, a IMD receives a signal that represents electrical activity within a heart of a patient following delivery of a stimulation pulse to the heart and reconfigures a filter state of a filter from an initial filter state to remove the polarization artifact from the electrical activity signal in order to determine whether a cardiac event, such as an evoked response has occurred. The medical device may, for example, when the filter of the medical device is a digital filter, recalculate the values of digital filter components using the present input value of the electrical activity signal as a direct current (DC) input value of the digital filter. While a digital filter may provide useful results, the filter adds cost to the implantable medical device. It is therefore desirable to develop additional or alternative methods that can be employed to further reduce or avoid polarization effects when detecting distinct waves in a cardiac signal.

DETAILED DESCRIPTION OF EXEMPLARY EMBODIMENTS

It will be apparent to a skilled artisan that elements or processes from one embodiment may be used in combination with elements or processes of the other embodiments, and that the possible embodiments of such methods, devices, and systems using combinations of features set forth herein is not limited to the specific embodiments shown in the Figures and/or described herein. Further, it will be recognized that the embodiments described herein may include many elements that are not necessarily shown to scale.

One or more embodiments of the present disclosure are directed to an implantable medical device (IMD) configured to avoid or reduce polarization effects associated with a cardiac signal. The IMD (e.g. implantable cardioverter-defibrillator (ICD)) is configured to deliver a ventricular pacing pulse. A signal is sensed in response to the ventricular pacing stimulus. A window is set over the sensed signal in order to obtain a set of data from the signal after a paced event. The window is delayed to avoid polarization effects. The delayed window begins about 30-60 ms after the paced event. The set of data extracted from the sensed signal can include a maximum amplitude (Max), a maximum time (Tmax) associated with the maximum amplitude, a minimum amplitude, and a minimum time associated with the minimum amplitude, all of which is within the delayed window of the signal. In the preferred embodiment, the window is delayed to search solely for the Max and Tmax while the search for the Min and Tmin uses a standard (i.e. non-delayed) window. With this configuration, both Tmax and Tmin are referenced to the time of the pacing pulse (Tpulse), not to the start time of the search window.

A determination is then made as to whether the maximum time Tmax is greater than the minimum time Tmin. A determination is then made as to whether the ventricular pacing stimulus is capturing the paced ventricle in response to determining whether the maximum time is greater than the minimum time. The present disclosure is able to achieve elimination of polarization effects without the need to employ a digital filter such as the digital filter used U.S. Pat. No. 7,089,049 to Kerver et al. Elimination of the digital filter reduces the cost of the IMD.

Figure 1:
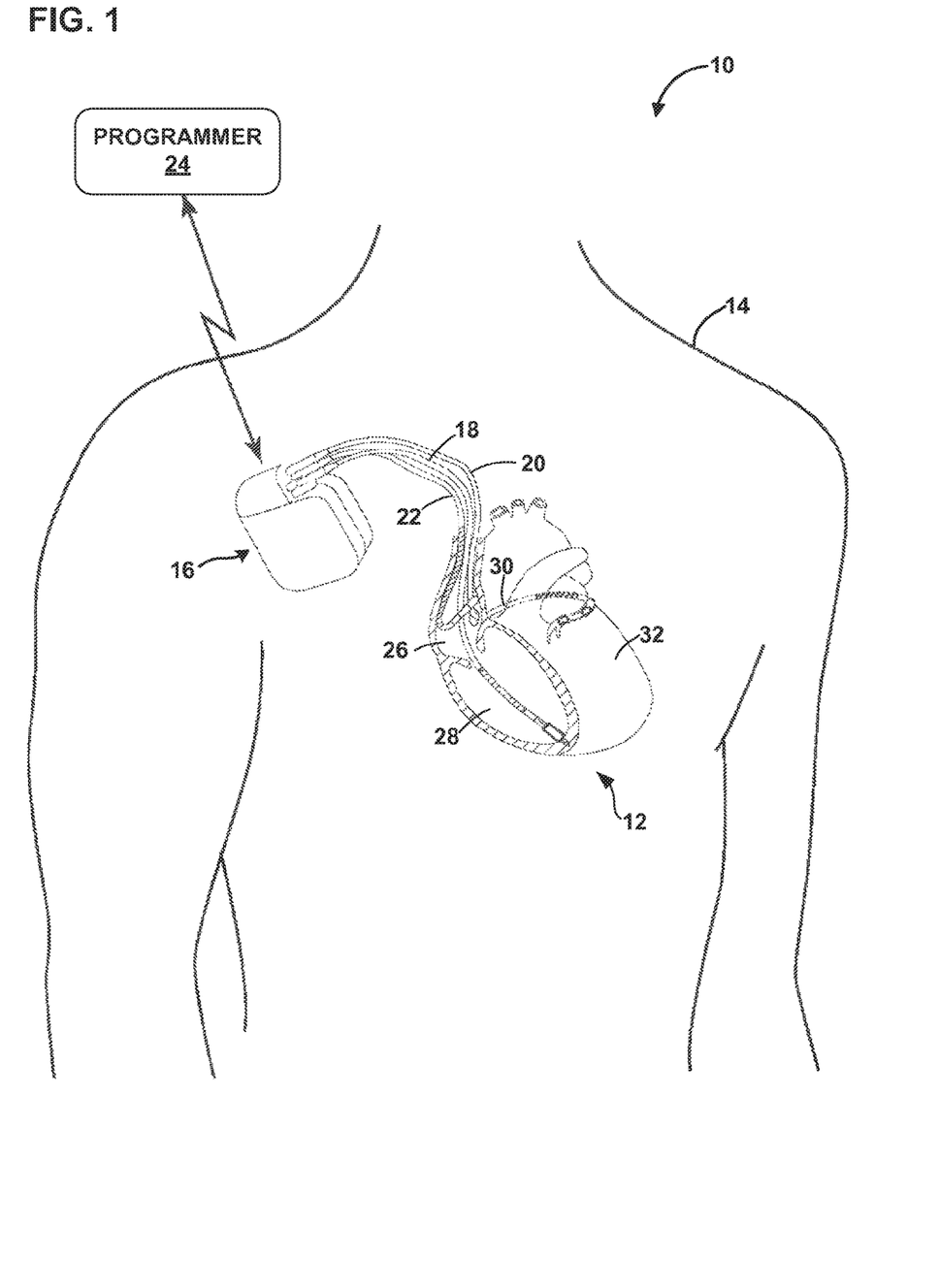
FIG. 1 is a diagram of an exemplary system including an exemplary implantable medical device (IMD).
Figure 2:
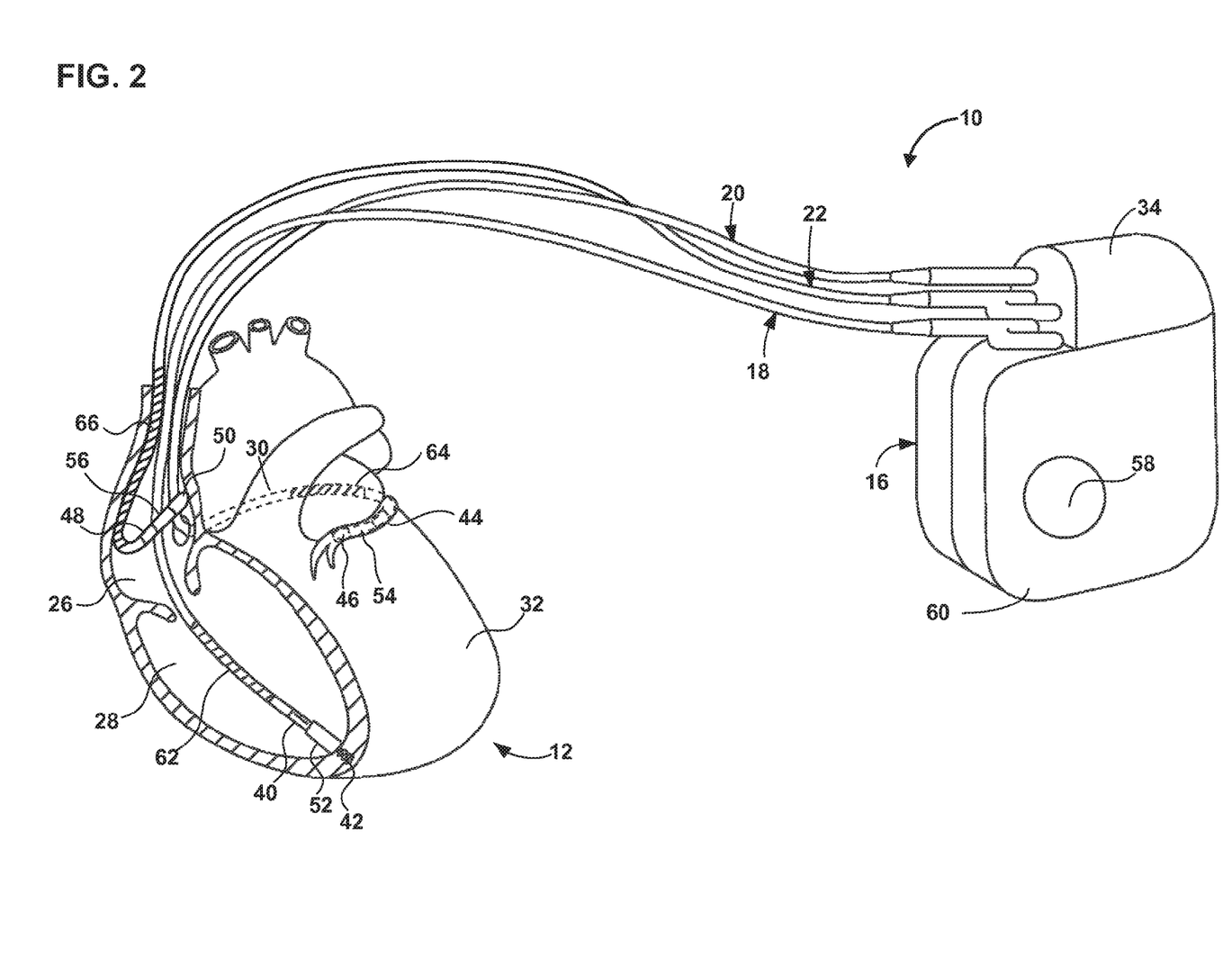
FIG. 2 is a diagram of the exemplary IMD of FIG. 1.
Figure 3A:
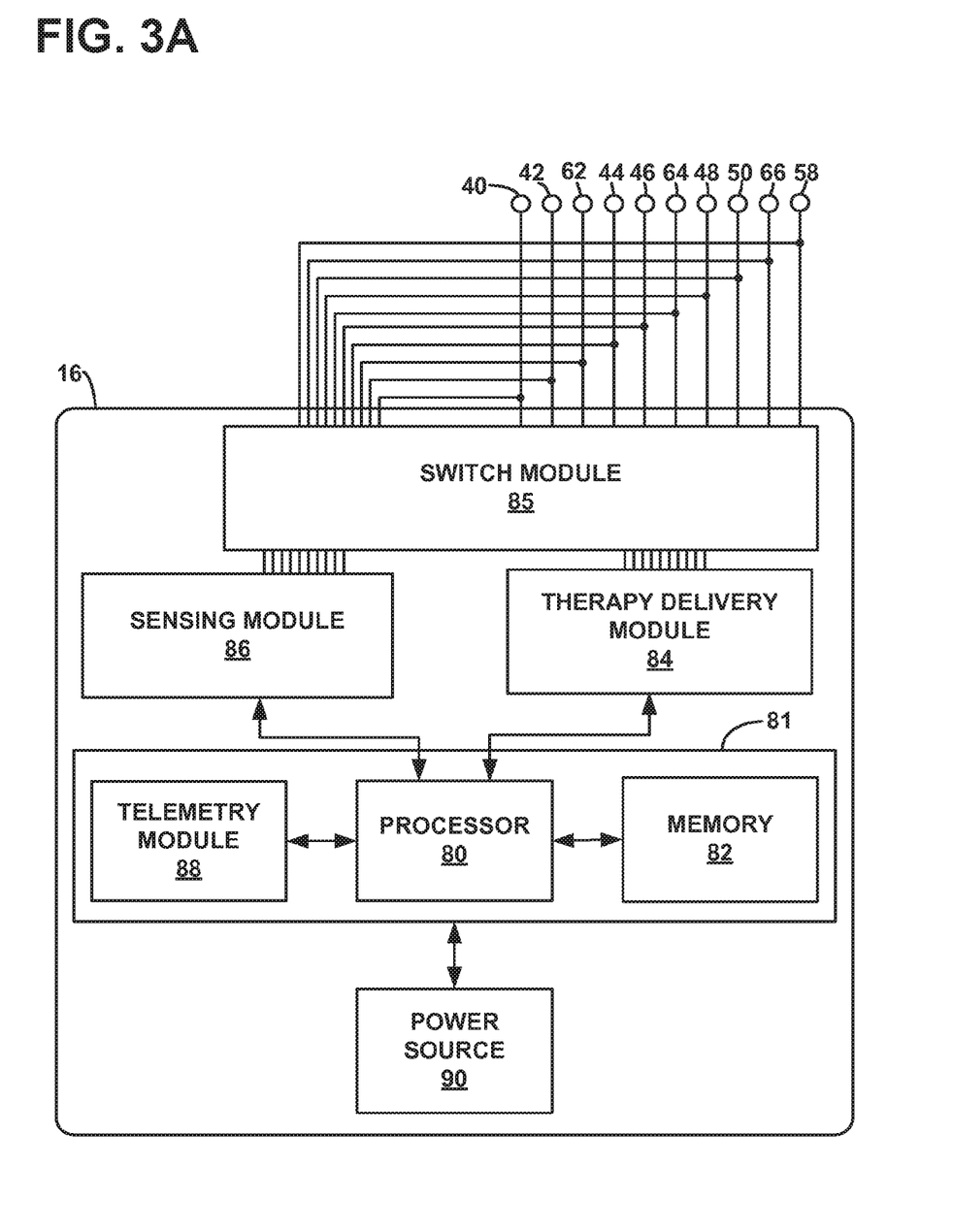
FIG. 3A is a block diagram of an exemplary IMD, e.g., the IMD of FIGS. 1-2.
Figure 3B:
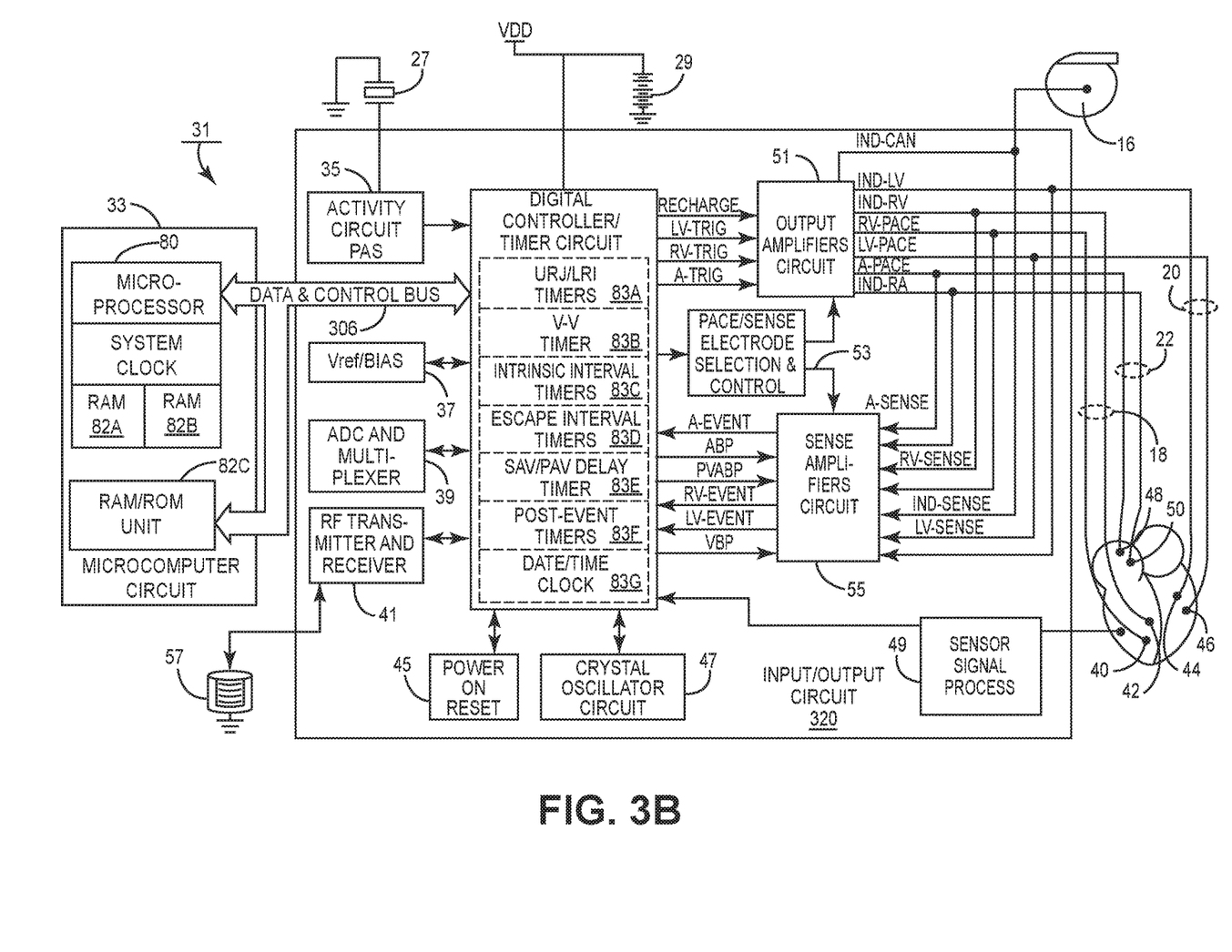
FIG. 3B is yet another block diagram of one embodiment of IMD (e.g. IPG) circuitry and associated leads employed in the system of FIG. 2 for providing three sensing channels and corresponding pacing channels that selectively functions in a ventricular pacing mode providing ventricular capture verification.

Presented below is a description of the IMD hardware (FIGS. 1-3). Thereafter, a description is presented of one or more processes (FIG. 4) used for reducing or avoiding polarization effects associated with a sensed cardiac signal.

FIG. 1 is a conceptual diagram illustrating an exemplary therapy system 10 that may be used to deliver pacing therapy to a patient 14. Patient 14 may, but not necessarily, be a human. The therapy system 10 may include an implantable medical device 16 (IMD), which may be coupled to leads 18, 20, 22 and a programmer 24. The IMD 16 may be, e.g., an implantable pacemaker, cardioverter, and/or defibrillator, that provides electrical signals to the heart 12 of the patient 14 via electrodes coupled to one or more of the leads 18, 20, 22.

The leads 18, 20, 22 extend into the heart 12 of the patient 14 to sense electrical activity of the heart 12 and/or to deliver electrical stimulation to the heart 12. In the example shown in FIG. 1, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12. Lead 22 is configured to acquire signals indicative of atrial fibrillation.

The IMD 16 may sense, among other things, electrical signals attendant to the depolarization and repolarization of the heart 12 via electrodes coupled to at least one of the leads 18, 20, 22. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., pulse wide, amplitude, voltage, burst length, etc. Further, the IMD 16 may be operable to use various electrode configurations to deliver pacing therapy, which may be unipolar or bipolar. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

In some examples, a programmer 24, which may be a handheld computing device or a computer workstation, may be used by a user, such as a physician, technician, another clinician, and/or patient, to communicate with the IMD 16 (e.g., to program the IMD 16). For example, the user may interact with the programmer 24 to retrieve information concerning one or more detected or indicated faults associated within the IMD 16 and/or the pacing therapy delivered therewith. The IMD 16 and the programmer 24 may communicate via wireless communication using any techniques known in the art. Examples of communication techniques may include, e.g., low frequency or radiofrequency (RF) telemetry, but other techniques are also contemplated.

FIG. 2 is a conceptual diagram illustrating the IMD 16 and the leads 18, 20, 22 of therapy system 10 of FIG. 1 in more detail. The leads 18, 20, 22 may be electrically coupled to a therapy delivery module (e.g., for delivery of pacing therapy), a sensing module (e.g., one or more electrodes to sense or monitor electrical activity of the heart 12 for use in determining effectiveness of pacing therapy), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 46 are located proximate to a distal end of the lead 20 and the bipolar electrodes 48, 50 are located proximate to a distal end of the lead 22.

The electrodes 40, 44, 48 may take the form of ring electrodes, and the electrodes 42, 46, 50 may take the form of extendable helix tip electrodes mounted retractably within the insulative electrode heads 52, 54, 56, respectively. Each of the electrodes 40, 42, 44, 46, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

The electrodes 40, 42, 44, 46, 48, 50 may further be used to sense electrical signals (e.g., morphological waveforms within electrograms (EGM)) attendant to the depolarization and repolarization of the heart 12. The electrical signals are conducted to the IMD 16 via the respective leads 18, 20, 22. In some examples, the IMD 16 may also deliver pacing pulses via the electrodes 40, 42, 44, 46, 48, 50 to cause depolarization of cardiac tissue of the patient's heart 12. In some examples, as illustrated in FIG. 2, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 46, 48, 50 may be used for unipolar sensing or pacing in combination with housing electrode 58. In other words, any of electrodes 40, 42, 44, 46, 48, 50, 58 may be used in combination to form a sensing vector, e.g., a sensing vector that may be used to evaluate and/or analysis the effectiveness of pacing therapy. An example of a configuration sensing and pacing may be seen with respect to U.S. patent application Ser. No. 13/717,896 filed Dec. 18, 2012, and assigned to the assignee of the present invention, the disclosure of which is incorporated by reference in its entirety herein as modified by preferably using a LVtip (i.e.

electrode 46)-Rvcoil (i.e. electrode 62) for the pacing vector and the sensing vector, respectively. It is generally understood by those skilled in the art that other electrodes can also be selected as pacing and sensing vectors. Electrode 44 and 64 refer to the third and fourth LV electrodes in the claims.

As described in further detail with reference to FIGS. 3A-3B, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity during pacing therapy (e.g., for use in analyzing pacing therapy effectiveness) and may be used in combination with any of electrodes 40, 42, 44, 46, 48, 50, 58. In at least one embodiment, the RV elongated electrode 62 may be used to sense electrical activity of a patient's heart during the delivery of pacing therapy (e.g., in combination with the housing electrode 58 forming a RV elongated, coil, or defibrillation electrode-to-housing electrode vector).

The configuration of the exemplary therapy system 10 illustrated in FIGS. 1-2 is merely one example. In other examples, the therapy system may include epicardial leads and/or patch electrodes instead of or in addition to the transvenous leads 18, 20, 22 illustrated in FIG. 1. Further, in one or more embodiments, the IMD 16 need not be implanted within the patient 14. For example, the IMD 16 may deliver defibrillation shocks and other therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 1-2. Still further, other therapy systems may include a single lead that extends from the IMD 16 into the right atrium 26 or the right ventricle 28, or two leads that extend into a respective one of the right atrium 26 and the right ventricle 28.

FIG. 3A is a functional block diagram of one exemplary configuration of the IMD 16. As shown, the IMD 16 includes a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. Memory 82 includes computer instructions related to capture management. An exemplary capture management module such as left ventricular capture management (LVCM) is briefly described in U.S. Pat. No. 7,684,863, which is incorporated by reference in its entirety. As to the delivery of pacing stimuli, capture management algorithms typically focus on sufficient energy delivery of a pacing stimulus.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control the therapy delivery module 84 to deliver electrical stimulus such as, e.g., pacing pulses with the amplitudes, pulse widths, frequency, or electrode polarities specified by the selected one or more therapy programs (e.g., pacing therapy programs, pacing recovery programs, capture management programs, etc.). As shown, the therapy delivery module 84 is electrically coupled to electrodes 40, 42, 44, 46, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 46, 48, 50, 58, 62, 64, 66.

For example, therapy delivery module 84 may deliver pacing stimulus (e.g., pacing pulses) via ring electrodes 40, 44, 48 coupled to leads 18, 20, and 22, respectively, and/or helical tip electrodes 42, 46, and 50 of leads 18, 20, and 22, respectively. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 46, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 46, 48, 50, 58, 62, 64, 66 to monitor electrical activity of the heart 12, e.g., electrocardiogram (ECG)/electrogram (EGM) signals, etc. The ECG/EGM signals may be used to analyze of a plurality of paced events. More specifically, one or more morphological features of each paced event within the ECG/EGM signals may be used to determine whether each paced event has a predetermined level of effectiveness. The ECG/EGM signals may be further used to monitor heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used to, e.g., sense electrical activity of the patient's heart (e.g., one or more electrical vectors of the patient's heart using any combination of the electrodes 40, 42, 44, 46, 48, 50, 58, 62, 64, 66). In some examples, the control module 81 may select the electrodes that function as sensing electrodes via the switch module within the sensing module 86, e.g., by providing signals via a data/address bus. In some examples, the sensing module 86 may include one or more sensing channels, each of which may include an amplifier.

In some examples, sensing module 86 includes a channel that includes an amplifier with a relatively wider pass band than the R-wave or P-wave amplifiers. Signals from the selected sensing electrodes that are selected for coupling to this wide-band amplifier may be provided to a multiplexer, and thereafter converted to multi-bit digital signals by an analog-to-digital converter for storage in memory 82 as an EGM. In some examples, the storage of such EGMs in memory 82 may be under the control of a direct memory access circuit. The control module 81 (e.g., using the processor 80) may employ digital signal analysis techniques to characterize the digitized signals stored in memory 82 to analyze and/or classify one or more morphological waveforms of the EGM signals to determine pacing therapy effectiveness. For example, the processor 80 may be configured to determine, or obtain, one more features of one or more sensed morphological waveforms within one of more electrical vectors of the patient's heart and store the one or more features within the memory 82 for use in determining effectiveness of pacing therapy at a later time.

If IMD 16 is configured to generate and deliver pacing pulses to the heart 12, the control module 81 may include a pacer timing and control module, which may be embodied as hardware, firmware, software, or any combination thereof. The pacer timing and control module may include one or more dedicated hardware circuits, such as an ASIC, separate from the processor 80, such as a microprocessor, and/or a software module executed by a component of processor 80, which may be a microprocessor or ASIC. The pacer timing and control module may include programmable counters which control the basic time intervals associated with DDD, VVI, DVI, VDD, AAI, DDI, DDDR, VVIR, DVIR, VDDR, AAIR, DDIR and other modes of single and dual chamber pacing. In the aforementioned pacing modes, "D" may indicate dual chamber, "V" may indicate a ventricle, "I" may indicate inhibited pacing (e.g., no pacing), and "A" may indicate an atrium. The first letter in the pacing mode may indicate the chamber that is paced, the second letter may indicate the chamber in which an electrical signal is sensed, and the third letter may indicate the chamber in which the response to sensing is provided.

Intervals defined by the pacer timing and control module within control module 81 may include atrial and ventricular pacing escape intervals, refractory periods during which sensed P-waves and R-waves are ineffective to restart timing of the escape intervals, and/or the pulse widths of the pacing pulses. As another example, the pacer timing and control module may define a blanking period, and provide signals from sensing module 86 to blank one or more channels, e.g., amplifiers, for a period during and after delivery of electrical stimulation to the heart 12. The durations of these intervals may be determined in response to stored data in memory 82. The pacer timing and control module of the control module 81 may also determine the amplitude of the cardiac pacing pulses.

During pacing, escape interval counters within the pacer timing/control module may be reset upon sensing of R-waves and P-waves. Therapy delivery module 84 (e.g., including a stimulation generator) may include one or more pacing output circuits that are coupled, e.g., selectively by the switch module 85, to any combination of electrodes 40, 42, 44, 46, 48, 50, 58, 62, or 66 appropriate for delivery of a bipolar or unipolar pacing pulse to one of the chambers of heart 12. The control module 81 may reset the escape interval counters upon the generation of pacing pulses by therapy delivery module 84, and thereby control the basic timing of cardiac pacing functions, including anti-tachyarrhythmia pacing.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as the programmer 24 as described herein with respect to FIG. 1. For example, under the control of the processor 80, the telemetry module 88 may receive downlink telemetry from and send uplink telemetry to the programmer 24 with the aid of an antenna, which may be internal and/or external. The processor 80 may provide the data to be uplinked to the programmer 24 and the control signals for the telemetry circuit within the telemetry module 88, e.g., via an address/data bus. In some examples, the telemetry module 88 may provide received data to the processor 80 via a multiplexer. In at least one embodiment, the telemetry module 88 may be configured to transmit an alarm, or alert, if the pacing therapy becomes ineffective or less effective (e.g., does not have a predetermined level of effectiveness).

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

FIG. 3B is yet another embodiment of a functional block diagram for IMD 16. FIG. 3B depicts bipolar RA lead 22, bipolar RV lead 18, and bipolar LV CS lead 20 without the LA CS pace/sense electrodes 28 and 30 coupled with an IPG circuit 31 having programmable modes and parameters of a bi-ventricular DDD/R type known in the pacing art. In turn, the sensor signal processing circuit 49 indirectly couples to the timing circuit 83 and via data and control bus to microcomputer circuitry 33. Optionally, sensor signal process 49 is coupled to another sensor such as an oxygenation sensors, pressure sensors, pH sensors and respiration sensors etc. The IPG circuit 31 is illustrated in a functional block diagram divided generally into a microcomputer circuit 33 and a pacing circuit 83. The pacing circuit includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 47 provides the basic timing clock for the pacing circuit 320, while battery 29 provides power. Power-on-reset circuit 45 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 320, while analog to digital converter ADC and multiplexer circuit 39 digitizes analog signals and voltage to provide real time telemetry if a cardiac signals from sense amplifiers 55, for uplink transmission via RF transmitter and receiver circuit 41. Voltage reference and bias circuit 37, ADC and multiplexer 39, power-on-reset circuit 45 and crystal oscillator circuit 47 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. Nos. 5,052,388 and 4,428,378. Similarly, the present invention may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the present invention may also be practiced in non-rate responsive pacemakers.

Data transmission to and from the external programmer is accomplished by means of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and Marker Channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by means of data and control bus 306 from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82C in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the atrial-left ventricular pace (A-LVp) delay (or atrial right ventricular pace (A-RVp delay) from a preceding A-EVENT or A-TRIG, a post-ventricular timer for timing post-ventricular time periods, and a date/time clock 83G.

The AV delay interval timer 83E is loaded with an appropriate delay interval for one ventricular chamber (i.e., either an A-RVp delay or an A-LVp delay as determined using known methods) to time-out starting from a preceding A-PACE or A-EVENT. The interval timer 83E triggers pacing stimulus delivery, and can based on one or more prior cardiac cycles (or from a data set empirically derived for a given patient).

The post-event timers 83F time out the post-ventricular time periods following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (or a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and indifferent electrodes (IND) to the RA pace pulse generator (and LA pace pulse generator if provided), RV pace pulse generator and LV pace pulse generator. Indifferent electrode means any electrode that has no interaction with a designated element. For example there is no interaction between the atrial electrodes and the LV electrode (i.e. no pacing, sensing, or even sub-threshold measurements) since that pathway has no value. If a RV electrode can interact with the LV electrode, then the RV electrode cannot be defined as being indifferent unless specifically defined as isolated from the LV electrode.

Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. As noted in the above-referenced, commonly assigned, '324 patent, it has been common in the prior art to use very high impedance P-wave and R-wave sense amplifiers to amplify the voltage difference signal which is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND_CAN electrode on lead 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND_CAN electrode on lead 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves. Skilled artisans will appreciate that the embodiments shown in FIGS. 1-3 are merely exemplary. For example, the implanted medical device may not include one or more of the leads shown in FIG. 1.

The present disclosure can find wide application to other implantable medical devices or possibly external medical devices that analyze electrical activity signals with post-pace artifacts, such as polarization artifacts. As previously stated, evoked responses from cardiac tissue are often difficult to detect due to polarization artifacts present on the sensing electrode employed to sense the electrical activity of the heart. The problem associated with polarization artifacts is especially prevalent in pacing systems that use the same lead to deliver the stimulation pulse and sense electrical activity of the heart after delivery of the stimulation pulse. Polarization of the pacing electrode is caused by accumulation of charge on an interface between the electrode and the cardiac tissue of the heart during delivery of a stimulation pulse.

Figure 4:
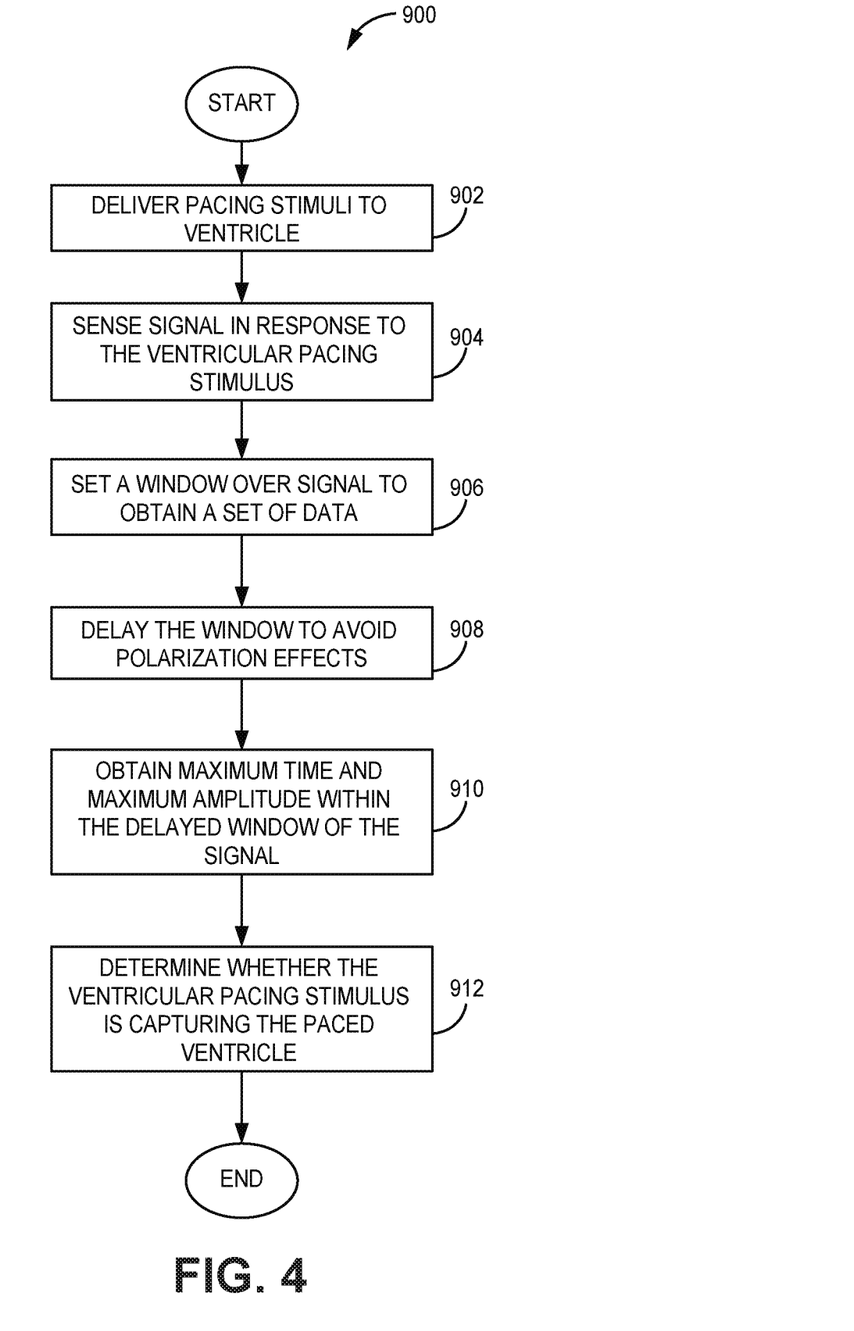
FIG. 4 is a flowchart of an exemplary process employed by an implantable medical device to reduce or eliminate polarization effects in order to detect an evoked response following delivery of a stimulation pulse.

FIG. 4 is a flowchart of an exemplary process employed by IMD 16 to reduce or eliminate polarization effects in order to detect an evoked response following delivery of a stimulation pulse. Method 900 begins at block 902 in which the IMD 16 delivers pacing stimuli to the ventricle through one or more electrodes associated with the IMD 16. At block 904, a signal is sensed by IMD 16 in response to the ventricular pacing stimulus.

Figure 5:
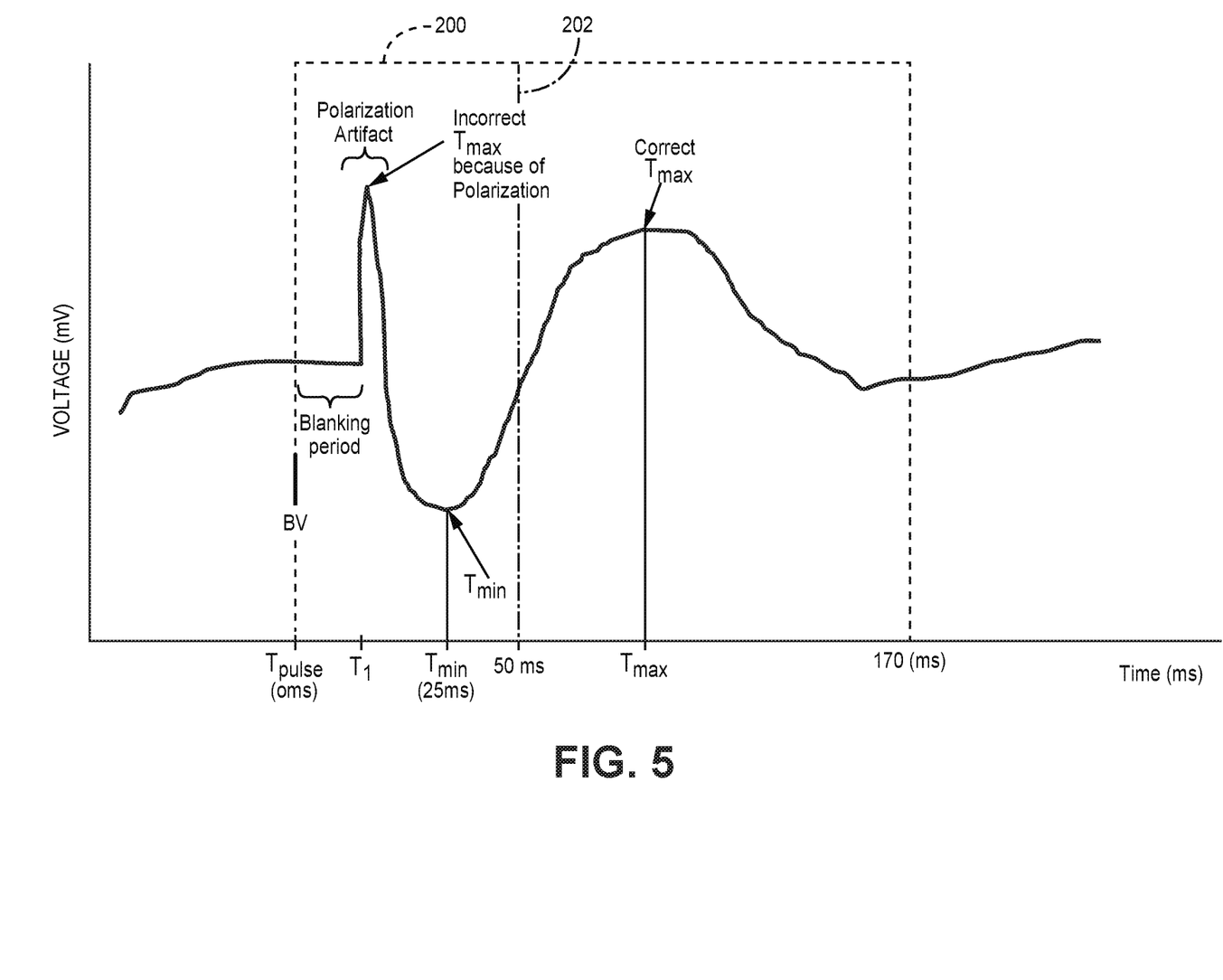
FIG. 5 is a graph that illustrates electrical activity signals with polarization artifact and the delay employed by the present disclosure to avoid the polarization artifact.

An exemplary sensed electrical activity signal, shown in FIG. 5, includes a positive polarization artifact as well as an evoked response signal, e.g., after delivery of a biventricular stimulation pulse (Tpulse) that does capture heart 12 of a patient.

Immediately after the blanking period, a positive polarization effect is displayed. A number of conventional IMDs incorrectly interpret the polarization artifact, with an amplitude of, for example, 2-20 mV as an evoked response from cardiac tissue. The present disclosure avoids or eliminates polarization effects by placing an analysis window (or sensing window) over the sensed signal at block 906, which is shown as the non-delayed window 200 in FIG. 5 (not drawn to scale) and then sliding the analysis window over the signal after a certain delay to obtain Max and Tmax. For the sake of more clearly describing the non-delayed window 200 and the delayed window 202, Tpulse is designated as Oms since Tpulse is used as a reference time.

The non-delayed window 200 starts at a reference time Tpulse and extends to 170 ms away from Tpulse. Non-delayed window 200 encompasses a hardware blanking period (i.e. 20 ms away from Tpulse until the end of the blanking period (T1), a positive polarization artifact immediately after the blanking period, Tmin at 25 ms away from Tpulse, a Max amplitude designated associated with the correctly identified Tmax, and the end (i.e. 170 ms) of the non-delayed window. The blanking period is an amount of time that the electrodes are "turned off" in order to prevent saturation due to an applied stimulation pulse, e.g., a pacing stimulation pulse or defibrillation shock.

The analysis or sensing window, which determines boundaries for extracting data from a sensed signal, is then delayed at block 908. The delayed window 202 is superimposed over the sensed signal, which can all be displayed on a graphical user interface to a user. The delayed window 202 is very different from the non-delayed window 200. While delayed window 202 has the same ending boundary (i.e. 170s) as the non-delayed window 200, delayed window 202 starts 50ms away from Tpulse which clearly excludes the polarization artifact. By excluding the polarization artifact, method 900 will be able to more correctly identify the evoked response from the cardiac tissue.

At block 910, data is extracted from the signal that is found within the delayed window 202. In the preferred embodiment, the set of data extracted from the signal within the delayed window solely includes Max and Tmax. Under the preferred embodiment scenario, Tmin and Min are extracted from the signal within the non-delayed window 200, which occurs before the analysis window is delayed to extract Max and Tmax. In one or more other embodiments, the set of data comprises a maximum amplitude (Max), a maximum time (Tmax) associated with the maximum amplitude, a minimum amplitude, and a minimum time associated with the minimum amplitude. Delay D can be any value between 30-60 milliseconds (ms) after Tpulse. In one or more other embodiments, Delay D can range from 30 ms to about 100 ms after Tpulse. Delay D, used in conjunction with an effective capture algorithm, may successfully bypass polarization effects.

Numerous other embodiments can be employed. For example, in the event of fast ventricular rates, there is considerable shortening of the QT interval, or the interval between depolarization and repolarization. To avoid picking up repolarization features like T-wave maximums or minimums, the analysis window for the effective capture algorithm may be shortened as a function of the ventricular cycle length. In one or more other embodiments, a median of last three (3) RR intervals is used for the cycle-length. From the ECG, the heart rate is measured using the R wave to R wave interval (RR interval). Thereafter, the analysis window is adjusted. Several examples are presented below. In one example, a median of a last three R-R intervals could be greater than or equal to 600 ms. Under this scenario, the analysis window is 167 ms.

In yet another example, a median of the last 3 R-R intervals may be between 500-600 ms. Under this scenario, the analysis window is shortened and is set equal to 130 ms.

In still yet another example, an analysis window is adapted for fast ventricular rates. By way of illustration, assume that a median of the last 3 R-R intervals is less than 500 ms. Under this scenario, the analysis window is substantially shortened to 100 ms.

In one or more other embodiments, the analysis window can be expressed as a linear function of the RR interval. More specifically, the analysis window can be expressed as a linear function of cycle-length. For example, the analysis window can be defined as follows:

Analysis window=a+b*(R-R) where a and b are constants. The value of "a" can range from 0-70 ms and value of "b" can range from 0.1-0.5.

In one or more embodiments, the EGM that is monitored is switched to a neighboring electrode. For example, assume that the Lvring to Rvcoil EGM is used to monitor for effective LV capture when pacing from Lvtip to Rvcoil. On one or more embodiments, during the daily effective capture test, the EGM amplitude is measured immediately after post-pace blanking. The EGM amplitude immediately after post-pace blanking is representative of the polarization effects. If the EGM amplitude has a large positive amplitude too large (e.g., greater than 3 mV), the adaptive heart rate algorithm can be disabled for 24 hours, as outlined in U.S. patent application 14/211,884 filed Mar. 14, 2014. In another embodiment, the results of the effective capture test at short paced A-V delays may be used to detect polarization.

At block 912, the processor 80 is configured to determine whether the ventricular pacing stimulus is capturing the paced ventricle in response to determining whether the maximum time is greater than the minimum time. There are many different methods that can be used to determine whether pacing stimuli has effectively captured cardiac tissue. An example of such a method may be seen with respect to U.S. patent application Ser. No. 13/707,366 filed Dec. 6, 2012, and assigned to the assignee of the present invention, the disclosure of which is incorporated by reference in its entirety herein. To determine if effective LV capture can occur under ideal conditions, an effective capture test (ECT) is performed periodically (e.g. daily, etc.), upon the direction of a user (e.g. while the patient sleeps such as at night time), or in response to consistent observation of ineffective capture. Generally, ideal conditions relate to delivering a pacing stimulus at an adequate amplitude and time.

The ECT test can be performed for LV only pacing or BV pacing. The manner in which the ECT is performed depends upon whether the patient is experiencing atrial fibrillation (AF). AF generally results in switching of pacing behavior to a pacing mode that does not track atrial activation (e.g., DDI, DDIR, WI, or VVIR pacing modes). When not in AF, the device generally is operating in a pacing mode that tracks atrial activation, such that SAV and PAV are relevant pacing timing parameters. For example, if the patient is not in AF, LV-only pacing employs a very short PAV (e.g. 10 ms) or SAV (e.g. 10 ms). Alternatively, if the patient is experiencing AF, LV-only pacing can employ an overdrive rate. Test beats (e.g. 5 test beats, etc.) are delivered to a ventricle to determine whether the ventricle was effectively captured in accordance with the criteria presented in FIG. 4 and the accompanying text. If, for example, 75% of the tested beats such as 4 of 5 beats are effectively captured, the ECT is passed for that day. Passing the ECT for that day means that effective capture is at least possible under ideal conditions. Effective capture by electrical stimuli occurs when at least 75% of the number of tested days (i.e., 31 out of 40 days) passed the ECT.

The BV test follows the LV test. For the BV test, a very short PAV or SAV is used along with the currently programmed W delay if the patient is not in AF, and an overdrive rate is employed if the patient is in AF. Again, 5 test beats are delivered with BV pacing, and 4 of 5 must pass effective LV capture. LV paced beat or BV paced beat is deemed to provide effective capture if the morphological features satisfy the effective capture test (ECT). The ECT can comprise one, two or three of the following relationships:

$$Tmax-Tmin>30ms \quad (1)$$

$$0.2<|Max-BL|/BL-Min|<5 \text{ or } (|Max-BL|/|Min-BL|\leq LL \text{ and } BL <|Min/8|) \quad (2)$$

and $$Tmin<60ms \text{ or } Max-Min>3.5mV \quad (3)$$

All timing parameters are measured from the time at which the pace is delivered.

This disclosure has been provided with reference to illustrative embodiments and is not meant to be construed in a limiting sense. As described previously, one skilled in the art will recognize that other various illustrative applications may use the techniques as described herein to take advantage of the beneficial characteristics of the apparatus and methods described herein. Various modifications of the illustrative embodiments, as well as additional embodiments of the disclosure, will be apparent upon reference to this description.

What is claimed is:

1. A method for reducing polarization effects after delivering pacing stimuli to a ventricle, comprising: delivering pacing stimuli employing a pacing pulse generator to deliver a ventricular pacing stimulus to a ventricle; employing a sense amplifier to sense sensing a signal in response to the ventricular pacing stimulus; employing a processor to obtain obtaining a set of data from the signal after a paced event, the set of data comprising a minimum amplitude, a minimum time associated with the minimum amplitude, a maximum amplitude, and a maximum time associated with the maximum amplitude and to determine determining whether the ventricular pacing stimulus is capturing the paced ventricle in response to determining whether the maximum time is greater than the minimum time.

2. The method of claim 1, further comprising employing the processor to set a delayed window following the paced event and wherein the steps of obtaining the maximum amplitude and the maximum time associated therewith occur within the delayed window.

3. The method of claim 2 wherein setting the delayed window involves an equation such that:
delayed window =a+b*(R-R) where a and b are constants, a value of "a" ranging from 0-70 milliseconds (ms) and a value of "b" ranging from 0.1-0.5.

4. The method of claim 2 wherein the delayed window begins about 30-100 ms after the paced event.

5. The method of claim 2 further comprising:
tracking a set of R-R intervals;
determining a median of the set of R-R intervals; and
setting the delayed window responsive to the determining the median of the set of R-R intervals.

6. The method of claim 1 further wherein the reduction of polarization effects occurs without using a digital filter on the sensed signal.

7. The method of claim 1 wherein a same electrode is used to deliver the pacing stimulus and to sense the signal.

8. A non-transitory machine-readable medium containing executable computer program instructions which when executed by a data processing system cause said system to perform a method comprising the steps of:
employing a pacing pulse generator to deliver a ventricular pacing stimulus to a ventricle;
employing a sense amplifier to sense a signal in response to the ventricular pacing stimulus;
employing a processor to obtain a set of data from the signal after a paced event, the set of data comprising a minimum amplitude, a minimum time associated with the minimum amplitude, a maximum amplitude, and a maximum time associated with the maximum amplitude and to determine whether the ventricular pacing stimulus is capturing the paced ventricle in response to determining whether the maximum time is greater than the minimum time.

9. The medium of claim 8, wherein the instructions further cause the processor to set a delayed window following the paced event and wherein the steps of obtaining the maximum amplitude and the maximum time associated therewith occur within the delayed window.

10. The medium of claim 9 wherein setting the delayed window involves an equation such that:
delayed window =a +b*(R-R) where a and b are constants, a value of "a" ranging from 0-70 milliseconds (ms) and a value of "b" ranging from 0.1-0.5.

11. The medium of claim 9 wherein the delayed window begins about 30-100 ms after the paced event.

12. The medium of claim 9 wherein the instructions further cause the system to:
track a set of R-R intervals; and
determine a median of the set of R-R intervals; and wherein
setting the delayed window is performed responsive to the determining the median of the set of R-R intervals.

13. The medium of claim 8 wherein the instructions cause the system to reduce of polarization effects without using a digital filter on the sensed signal.

14. The medium of claim 8 wherein the instructions cause the system to employ a same electrode to deliver the pacing stimulus and to sense the signal.

15. A method for reducing polarization effects after delivering pacing stimuli to ventricle, comprising:
employing a pacing pulse generator to deliver a ventricular pacing stimulus to a ventricle;
employing a sense amplifier to sense a signal in response to the ventricular pacing stimulus;
employing a processor to:
obtain a non-delayed window to obtain a set of data from the signal after a paced event, the set of data comprising a minimum amplitude, and a minimum time associated with the minimum amplitude;
set a delayed window to avoid polarization effects to obtain another set of data comprising a maximum amplitude, and a maximum time associated with the maximum amplitude, the maximum time and the maximum amplitude located within the delayed window of the signal; and
determine whether the ventricular pacing stimulus is capturing the paced ventricle in response to determining whether the maximum time is greater than the minimum time.

16. The method of claim 15 wherein setting the delayed window involves an equation such that:
delayed window =a+b*(R-R) where a and b are constants, a value of "a" ranging from 0-70 milliseconds (ms) and a value of "b" ranging from 0.1-0.5.

17. The method of claim 15 wherein the delayed window begins about 30-100 ms after the paced event.

18. The method of claim 15 wherein elimination of polarization effects occurs without using a digital filter on the sensed signal.

19. The method of claim 18 wherein a same electrode is used to deliver pacing stimuli and sense the signal.

20. The method of claim 15 further comprising:
tracking a set of R-R intervals;
determining a median of the set of R-R intervals; and
setting the delayed window.

21. A method for reducing polarization effects after delivering pacing stimuli to ventricle, comprising:
employing a pacing pulse generator to deliver a ventricular pacing stimulus to a ventricle;
employing a sense amplifier to sense a signal in response to the ventricular pacing stimulus;
employing a processor circuit to obtain a set of data from the signal after a paced event, the set of data comprising a minimum amplitude, a minimum time associated with the minimum amplitude, a maximum amplitude, and a maximum time associated with the maximum amplitude and to determine whether the ventricular pacing stimulus is capturing the paced ventricle in response to determining whether the maximum time is greater than the minimum time.

* * * * *